(12) United States Patent
Platscher et al.

(10) Patent No.: US 8,513,446 B2
(45) Date of Patent: Aug. 20, 2013

(54) STABLE CRYSTAL MODIFICATIONS OF DOPC

(75) Inventors: Michael Platscher, Schlatt (CH); Alfred Hedinger, Thayngen (CH)

(73) Assignee: Merck Patent GmbH, Darmstadt (DE)

( * ) Notice: Subject to any disclaimer, the term of this patent is extended or adjusted under 35 U.S.C. 154(b) by 273 days.

(21) Appl. No.: 12/995,991

(22) PCT Filed: May 13, 2009

(86) PCT No.: PCT/EP2009/003398
§ 371 (c)(1),
(2), (4) Date: Dec. 20, 2010

(87) PCT Pub. No.: WO2009/146779
PCT Pub. Date: Dec. 10, 2009

(65) Prior Publication Data
US 2011/0086091 A1    Apr. 14, 2011

(30) Foreign Application Priority Data

Jun. 6, 2008 (EP) .................................... 08010331

(51) Int. Cl.
*A61K 9/127* (2006.01)

(52) U.S. Cl.
USPC ................. 554/80; 554/82; 554/83; 977/773; 977/915

(58) Field of Classification Search
USPC .................. 424/184, 450; 514/78; 977/773, 977/915; 554/80, 82, 83
See application file for complete search history.

(56) References Cited

U.S. PATENT DOCUMENTS
2006/0067998 A1 * 3/2006 Kurzrock et al. ............. 424/450

FOREIGN PATENT DOCUMENTS
DE        2647395        10/1976

OTHER PUBLICATIONS

International Search Report of PCT/EP2009/003398, Date of Completion Jul. 27, 2009, Date of Mailing Aug. 3, 2009.
Hishida et al: "Stacking structures of dry phospholipids films on a solid substrate," Colloids and Surfaces. A, Physicachemical and Engineering Aspects, Elsevier, Amsterdam, NL Bd. 284-285, Aug. 15, 2006, Seiten 444-447, XP005496833 ISSN: 0927-7757.
William M Merritt et al: Effect of Interleukin-8 Gene Silencing With Liposome-Escapsulated Small Interfering RNA on Ovarian Cancer Cell Growth, Sood et al. Journal of the National Cancer Institute, 2008, 100, pp. 359-372.
Ichihara et al.: Synthesis of phosphatidylcholine: An improved method without using the cadmium chloride complex of sn-glycero-3-phosphocholine, Chemistry and Physics of Lipids 2005, 137 (1-2) pp. 94-99.
Roodsari et al., Lewis et al.: "A New Approach to the Stereospecific Synthesis of Phospholipids. The Use of L-Glyceric Acid for the Preparation of Diacylglycerols", Phosphatidylcholines, and Related Derivatives, Journal of Organic Chemistry (1999), 64 (21) pp. 7727-7737.
Lewis et al., "Evidence of Targeted Gene Delivery to Hep G2 Hepatoma Cells in Vitro", Biochemistry (1988), 27 (3), pp. 880-887.

(Continued)

*Primary Examiner* — Deborah D Carr
(74) *Attorney, Agent, or Firm* — Millen, White, Zelano & Branigan, P.C.

(57) ABSTRACT

The invention relates to stable crystal modifications of (R,S)-, (R)- and (S)-DOPC, to a process for the preparation of these modifications, and to the use thereof as constituent for the preparation of medicaments.

24 Claims, 11 Drawing Sheets

(XRD spectrum of type I DOPC)

(56) References Cited

OTHER PUBLICATIONS

Lewis et al., "Effect of Fatty Acyl Chain Length and Structure on the Lamellar Gel to Liquid-Crystalline and Lamellar to Reversed Hexagonal Phase Transitions of Aqueous Phosphatidylethanolamine Dispersions," Biochemistry (1989) 28(2) pp. 541-548.

Baer et al., L-α-(Dioleoyl)lecithin* An Alternate Route to Its Synthesis, Biochemistry (1962), 1(3), pp. 518-521.

Hishida et al., "Stacking structures of dry phospholipids films on a solid substrate," Colloids and Surfaces A: Physiochem. Eng. Aspects pp. 284-285(2006) pp. 444-447, XP005496833.

* cited by examiner

Fig. 1 (XRD spectrum of type I DOPC)

Fig. 2 (XRD spectrum of lyophilised DOPC)

Fig. 3 (XRD spectrum of waxy DOPC)

Fig. 4 (Type I DOPC crystals)

Fig. 5 (Waxy DOPC)

Fig. 6 (Type I DOPC crystals under the polarising microscope)

Fig. 7 (Lyophilised DOPC under the polarising microscope)

Fig. 8 (Waxy DOPC under the polarising microscope)

Fig. 9 (Melting behaviour of type I DOPC)

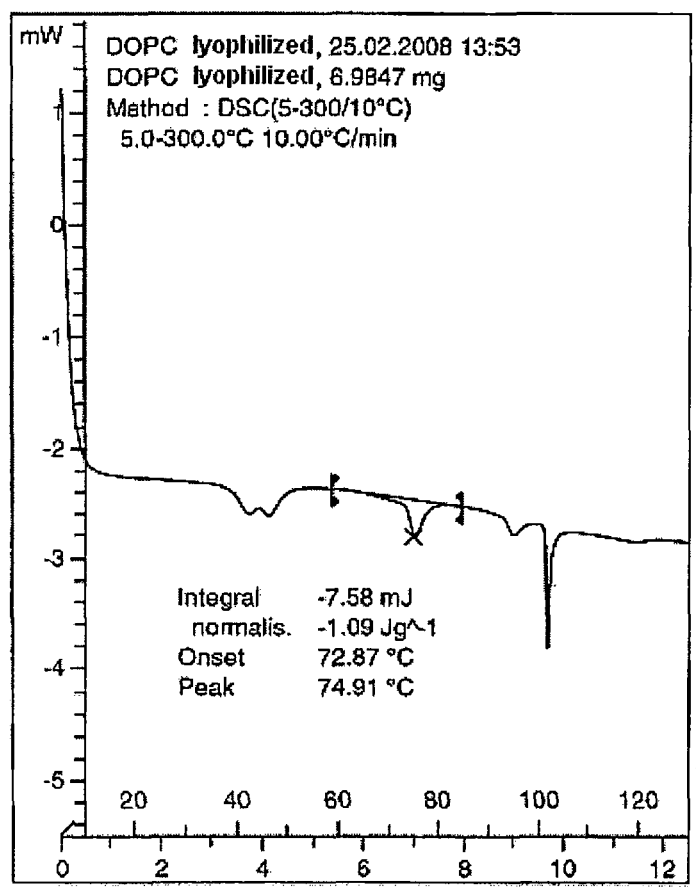
Fig. 10 (Melting behaviour of lyophilised DOPC)

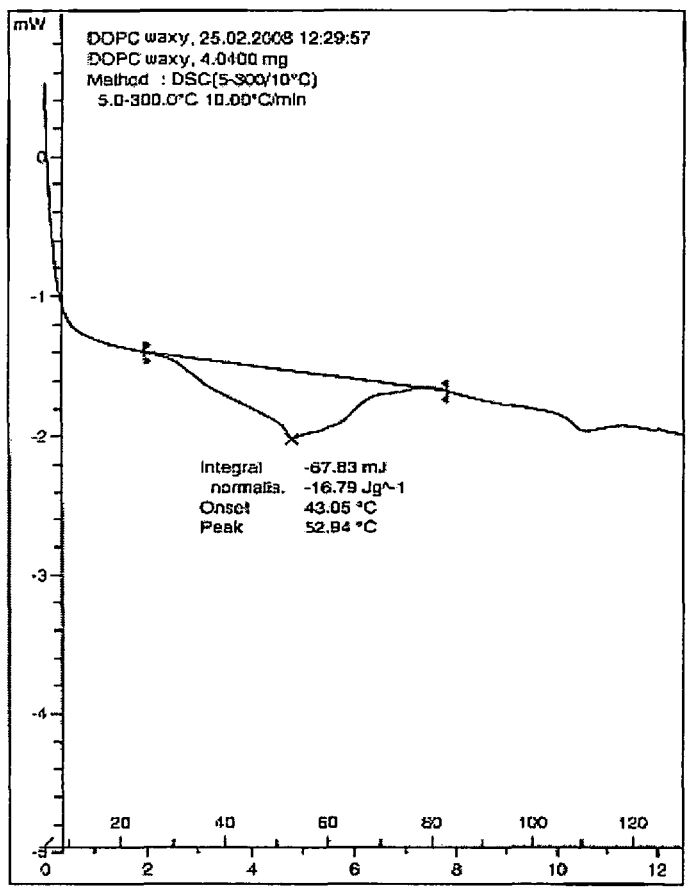
Fig. 11 (Melting behaviour of waxy DOPC)

STABLE CRYSTAL MODIFICATIONS OF DOPC

The present invention relates to crystal modifications of DOPC, to processes for the preparation thereof, and to the use thereof for the preparation of pharmaceutical compositions.

DOPC above and below refers to naturally occurring 1,2-dioleoyl-sn-glycero-3-phosphocholine, also referred to as 1,2-dioleoyl-sn-glycero-3-phosphatidylcholine, 1,2-dioleoyl-sn-glycero-3-phosphorylcholine, (R)-2,3-bis(oleoyloxy)propyl-2-(trimethylammonio)ethyl phosphate, 1,2-dioleoyl-L-α-lecithin or,
(R)-DOPC
the non-naturally occurring enantiomer thereof 2,3-dioleoyl-sn-glycerol-1-phosphocholine,
racemic (R,S)-DOPC, and other mixtures of the above-mentioned enantiomers.

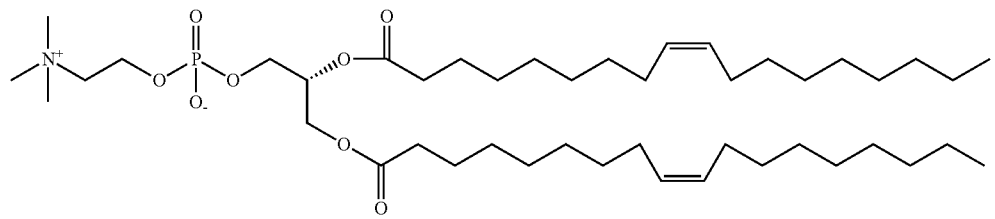

| | |
|---|---|
| $C_{44}H_{84}NO_8P$, | $M_W$ 786.11 |
| CAS numbers: | 4235-95-4 (R form) and 84366-67-6 (S form) |

Liposomes are synthetic multilayered vesicles (spherical in closed membranes) comprising ambiphilic substances, usually natural lipids, in which both hydrophilic substances can be encapsulated in the aqueous interior and also lipophilic substances can be incorporated into the interior of the lipid membrane.

They are employed, in particular, in cosmetics and in medicine, especially in dermatology. In particular, vitamins, coenzymes, skin-protection agents and sunscreens are embedded here. Liposomes are generally applied topically.

However, liposomes are increasingly achieving further importance in pharmaceutical technology since parenteral administration of liposomes enables more specific organ distribution to be achieved than if the active compounds are used in freely dissolved form.

Thus, U.S. 2006/0067998 A1 discloses a method in which a colloidally encapsulated formulation which comprises curcumin or a curcumin derivative as active substance is administered for the treatment or prevention of cancer diseases. Suitable formulations comprise both lipid-based colloidal systems and also polymeric colloidal systems, such as, for example, liposomes, nanoparticles, microparticles or copolymer micelles formed from block polymers.

If DNA-, RNA- or proteins are included, lipoplexes are obtained.

Nanoparticles (nanoparts) are particles of approximately the same size as liposomes, but which do not have a water phase, but instead an oil phase or a solid core in their interior. They are particularly suitable for the encapsulation of lipophilic substances.

Microemulsions are colloidally disperse, single-phase systems comprising aqueous, lipid-like and surfactant-like components. They have a particle size of 1-500 nm and behave in a similar way to liquids.

The solubilising effect in the applications described above is of very major importance, in particular, in connection with the normally low-solubility peptide-like active compounds, nucleotides, vaccines and other biopharmaceuticals.

In addition, the degradation of the active compounds in the body can be slowed and a sustained-release effect achieved in this way.

(R)-DOPC belongs to the class of naturally occurring, zwitterionic phosphocholines. Liposomes comprising zwitterionic lipids have a neutral surface, alone or combined with other phosphocholines or other uncharged, lipid-like compounds.

However, the ability of DOPC-based liposomes and lipoplexes to penetrate into cells and thus to transport the active compounds included in them into the cell interior (transfection) is particularly important. Such liposomes often comprise charged lipids, in particular cationic lipids. However, applications in which the lipoplexes consist exclusively of DOPC have also been published, for example by Sood et al. in the Journal of the National Cancer Institute (2008), 100, 359-372.

All these properties also make DOPC very interesting for cancer therapy. Due to these properties, it offers the possibility of administering RNA, DNA or conventional cytostatics included in DOPC liposomes.

Medical, in particular parenteral applications make extremely high requirements of the quality and purity of the active compounds and assistants used. Thus, there are very strict regulations regarding the preparation, reproducibility of preparation and by-product profile of these compounds on the part of the authorities. In the case of substances administered parenterally, microbiological impurities due to pathogenic germs and endotoxins additionally have to be strictly avoided and controlled.

DOPC is unstable at room temperature and is therefore difficult per se to prepare in acceptable purity so that it is suitable for use for the preparation of a medicament formulation.

Like all lipids which carry oleic acid radicals, such as, for example, the natural phospholipids POPC and DOPE, DOPC is very oxidation-sensitive. However, the oxidation products of unsaturated fatty acid derivatives generally have high toxicity.

Suitable preparation and purification methods are required here. DOPC is, for example, in the form of a lyophilisate or waxy solid and therefore can only be obtained in adequate quality with great difficulty industrially.

The conventional methods for overcoming the instability, such as, for example, the addition of antioxidants in the form of tocopherol or reduced L-glutathione, greatly restrict the general usability of DOPC since interactions with the active compounds later to be embedded cannot be excluded. Complete exclusion of oxygen during preparation, storage and use is virtually impossible or can only be achieved with very great effort.

Thus, the manufacturer generally recommends that lyophilised DOPC be stored under a protective gas at −20° C. and only guarantees a shelf life of about 12 months. Although a longer shelf life is guaranteed for waxy DOPC, an oxidation protection is added, and storage must likewise take place at −20° C.

Both lyophilised and waxy DOPC have very high amorphous contents.

Besides its oxidatidation sensitivity, this amorphous DOPC is also extremely hygroscopic and deliquesces within an extremely short time at normal atmospheric humidity levels to give a greasy film. In addition, waxy DOPC can only be comminuted with difficulty and, like lyophilised DOPC, can only be weighed out with difficulty. This makes handling of this compound much more difficult.

The literature only discloses various synthetic routes for the preparation of amorphous DOPC:

Ichihara et al., Chemistry and Physics of Lipids (2005), 137 (1-2), 94-99, outline the synthesis of DOPC from SN-glycero-3-phosphocholine (GPC).

Roodsari et al., Journal of Organic Chemistry (1999), 64(21), 7727-7737, describe the total synthesis of DOPC starting from trityl glycerol.

Many other publications on the synthesis and use of DOPC have appeared, but none describes crystalline material.

Lewis et al., Biochemistry (1988), 27(3), 880-7, and Biochemistry (1989), 28(2), 541-8, report on lyophilised DOPC.

Baer and Kindler in Biochemistry (1962), 1(3), 518-21, refer to waxy DOPC.

Lekim, Biedermann and Ghyczy, DE 2647395, describe generically the purification of GPC esters by crystallisation, but the explicit crystallisation of DOPC is not described.

Racemic DOPC can be obtained from racemic starting materials analogously to the processes described for the enantiomers.

In addition, none of the many publications gives a melting point for DOPC.

The object of the present invention is therefore to provide DOPC in high purity, if possible in crystalline form. A further object of the present invention is to provide this compound with a long shelf life and good handling properties, so that it can be employed for the preparation of pharmaceutical formulations. There is furthermore a strong need for a reproducible process for the preparation of stable forms of DOPC which can be carried out on an industrial scale.

Surprisingly, it has now been found through experiments that both racemic and also enantiomerically pure, crystalline DOPC having high chemical purity and excellent stability can be obtained in a simple manner. The crystalline products obtained in this way are stable for a virtually unlimited time at room temperature under a protective gas.

Crystalline DOPC is also produced as an easily handled loose material having improved hygroscopicity.

They are therefore suitable as constituent of or starting material for the preparation of medicament forms.

The present invention accordingly relates to stable crystal modifications of DOPC enantiomers and to mixtures of the enantiomers having the same crystal form.

The stable crystal modifications can be in crystalline and partially crystalline form. They have a never previously achieved purity of >98% together with a never previously achieved stability of >99%, based on the initial value, after storage for 12 months with exclusion of air at 40° C. and 75% relative atmospheric humidity and after 18 months at 25° C. and 60% relative atmospheric humidity (without addition of oxidation protection, in this respect see Table 1). The DOPC crystal modifications have a content of less than 1 equivalent of water or solvent of crystallisation per equivalent of DOPC.

Enantiomerically pure DOPC is, for example, in the type I crystal modification and exhibits medium-sharp bands in X ray powder diffraction measurements (in this respect see FIG. 1 and Table 2). Selected 2 theta values for the various crystal modifications are at 3.6, 5.3, 18.3, 19.3 and 21.7 (type I), measured with Cu Kα radiation. Slight differences of individual bands from these values may occur if different instruments or recording methods, such as reflection or transmission, or capillary or window, are selected, or if different recording conditions with respect to atmospheric humidity or temperature prevail.

Some of the crystal modifications have a very high crystalline content, which is evident in an enthalpy of melting of greater than 48 J/g. The melting point of the crystal modifications is generally above 60° C. (FIG. 9).

In addition, the crystal modifications according to the invention are produced as an easily handled loose material (FIG. 4). The crystalline character and becomes clear under the polarising microscope (FIG. 6).

Mixtures of the crystalline DOPC enantiomers, such as, for example, crystalline racemate, may also have the same XRD spectra.

The invention furthermore relates to a process for the preparation of DOPC crystal modifications, which is characterised in that DOPC is crystallised from an aprotic medium. Aprotic media which can be used for this purpose are aprotic solvents or mixtures thereof. The aprotic medium may also comprise a small proportion of protic solvents, such as, for example, water. In exceptional cases, 25% by weight of protic solvents may also be present under suitable conditions. The crystallisation of DOPC can be carried out here directly from the reaction solution without prior purification. Crystalline DOPC can likewise be obtained by recrystallisation of amorphous, partially crystalline or crystalline material.

Suitable aprotic solvents are, in particular, ethers, such as, for example, tetrahydrofuran, methyltetrahydrofuran and dioxane, esters, such as, for example, ethyl formate, methyl acetate, ethyl acetate, propyl acetate, isopropyl acetate, butyl acetate, isobutyl acetate, dimethyl carbonate, diethyl carbonate and 1,3-dioxolidin-2-one, ketones, such as, for example, acetone, 2-butanone, methyl isobutyl ketone, methyl isopropyl ketone, and nitriles, such as, for example, acetonitrile.

Protic solvent additions typically consist of alcohols, such as, for example, methanol, ethanol, n-propanol, iso-propanol, n-butanol, isobutanol, 2-butanol, tert-butanol, 3-methyl-1-butanol, ethylene glycol, methoxyethanol, ethoxyethanol, water or mixtures thereof.

The crystallisation of the DOPC modifications is generally carried out specifically by slow cooling of the prepared solution to temperatures below 30° C. The crystals form either spontaneously or through inoculation with the corresponding DOPC crystal modification.

The various DOPC crystal modifications can be converted into one another. The conversions can be achieved by temperature treatments of the isolated crystal modifications at elevated temperature or by lengthy stirring of their suspensions under crystallisation conditions.

The use of amorphous or partially crystalline DOPC as starting material for the recrystallisation in the process described gives essentially crystalline DOPC having a never previously achieved purity together with a never previously achieved stability.

The invention also relates to the use of crystalline DOPC for the preparation of medicament formulations, since crystalline DOPC has excellent stability in solid form under the given conditions and constant and very good quality over a virtually unrestricted period.

The invention consequently furthermore also relates to the pharmaceutical compositions resulting from the use of the DOPC forms claimed. These can be, for example, in the form of liposomes, lipoplexes, microemulsions and nanoparticles and comprise, for example, an active compound from the group of the peptides, nucleotides, vaccines and cytostatics.

The present description enables the person skilled in the art to use the invention in its full scope. Even without further comments, it is therefore assumed that the person skilled in the art will be able to utilise the above description in the broadest scope. The present description consequently enables the person skilled in the art to use and carry out the invention in its full scope.

In the case of any lack of clarity, it goes without saying that the publications and patent literature cited should be utilised. Accordingly, these documents are regarded as part of the disclosure content of the present description.

For better understanding and in order to illustrate the invention, examples are given below which are within the scope of protection of the present invention. These examples also serve to illustrate possible variants. Owing to the general validity of the inventive principle described, however, the examples are not suitable for reducing the scope of protection of the present application to these alone.

The temperatures given in the examples and description and in the claims are always in ° C. Unless indicated otherwise, content data are given in % by weight.

It furthermore goes without saying to the person skilled in the art that, both in the examples given and also in the remainder of the description, the component amounts present in the compositions always only add up to 100% by weight or 100 mol %, based on the composition as a whole, and cannot exceed this, even if higher values could arise from the percent ranges indicated. Unless indicated otherwise, % data are % by weight, with the exception of ratios, which are shown in volume data.

BRIEF DESCRITION OF DRAWINGS

FIG. 10 Illustrates Melting behaviour of lyophilised DOPC by differential scanning calorimetry (DSC) measurements; and FIG. 11 Illustrates Melting behaviour of waxy DOPC by differential scanning calorimetry (DSC) measurements.

EXAMPLES FOR ILLUSTRATION OF THE INVENTION

Example 1

Crystallisation of (R)-DOPC 200 g of amorphous (R)-DOPC are dissolved in 1700 ml of acetonitrile at 25° C. The solution is cooled to −10° C. at 0.1° C./min. Crystallisation commences at 10° C. When crystallisation is complete, the product is isolated by filtration and dried in vacuo. The yield of crystalline (R)-DOPC is 180 g (90%).

The crystal modifications (R,S)- and (S)-DOPC can be obtained in the same way.

Example 1a

Recrystallisation of DOPC From Ethyl Acetate 20.0 g of DOPC are dissolved in 100 ml of ethyl acetate at 35° C. The solution is cooled rapidly to 20° C. and then to −10° C. at a rate of 0.01° C./min, during which crystallisation commences. The crystallisate is filtered off and dried at room temperature in vacuo. The yield is 19.6 g of crystalline DOPC (98.1% of theory). At a heating rate of 5° C./min, the product exhibits a melting point of 71° C. and an enthalpy of melting of 49.4 J/g.

Example 2

Stabilities

In order to determine the stability of crystalline DOPC, the substances are stored together with comparative samples at 25° C. and 60% relative humidity and at 40° C. and 75% relative humidity with exclusion of air. The residual content of DOPC is measured at periodic intervals and indicated compared with the initial value.

Purity and content of DOPC are determined by HPLC.

For the type I crystal modification, the following values were found:

TABLE 1

| | Stability of type I crystalline (R)-DOPC | | | |
|---|---|---|---|---|
| Storage time | 25° C./60% relative humidity | | 40° C./75% relative humidity | |
| in months | % by weight | Area-% | % by weight | Area-% |
| 0 | 100.0 | 100.0 | 100.0 | 100.0 |
| 3 | 100.9 | 100.0 | 100.0 | 99.9 |
| 6 | 99.3 | 100.0 | 98.4 | 99.8 |
| 9 | 100.8 | 100.0 | 99.8 | 99.8 |
| 12 | 100.4 | 99.7 | 99.5 | 99.7 |
| 18 | 100.6 | 99.8 | — | — |

Example 3

X-Ray Powder Diffraction Patterns

In order to characterise the DOPC crystal modifications, X-ray powder diffraction patterns (XRD diffraction spectra)

of these substances are recorded. For comparative purposes, X-ray powder diffraction patterns (XRD diffraction spectra) of lyophilised and waxy DOPC variants are also recorded.

For type I DOPC crystal modifications, relatively high-resolution spectra with medium-sharp bands are obtained for lipids. The spectra indicate high crystalline contents. No amorphous components are visible under the polarising microscope.

Figure 1:
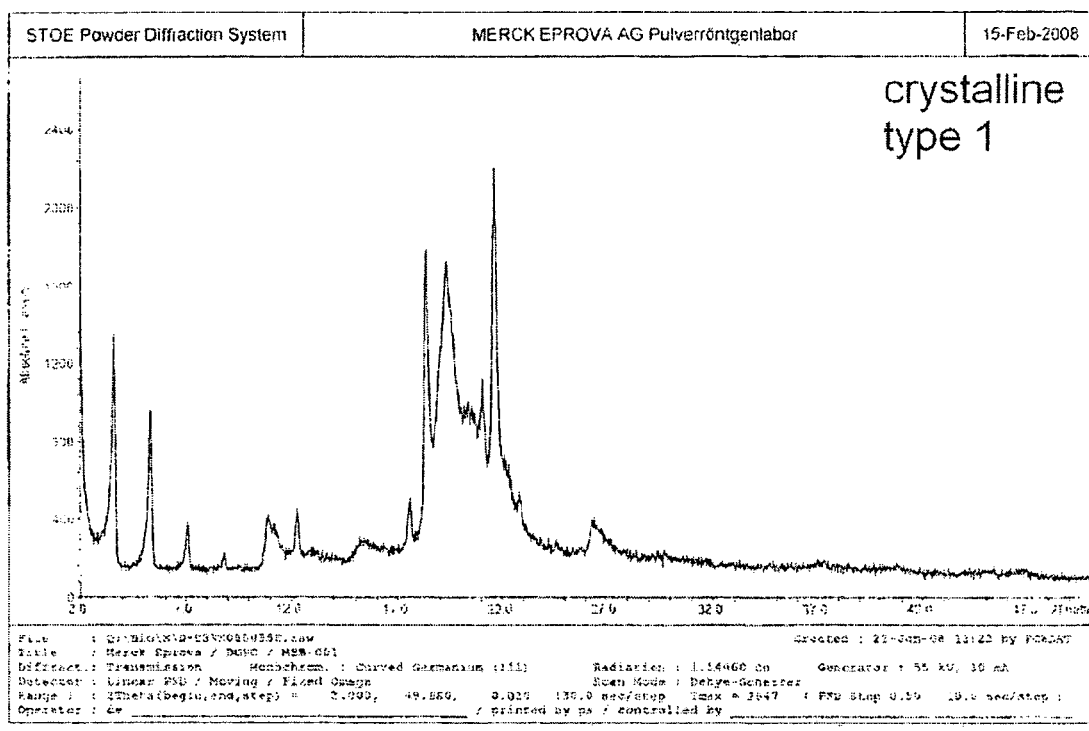
FIG. 1 Illustrates an XRD spectrum of type I DOPC.
Figure 2:
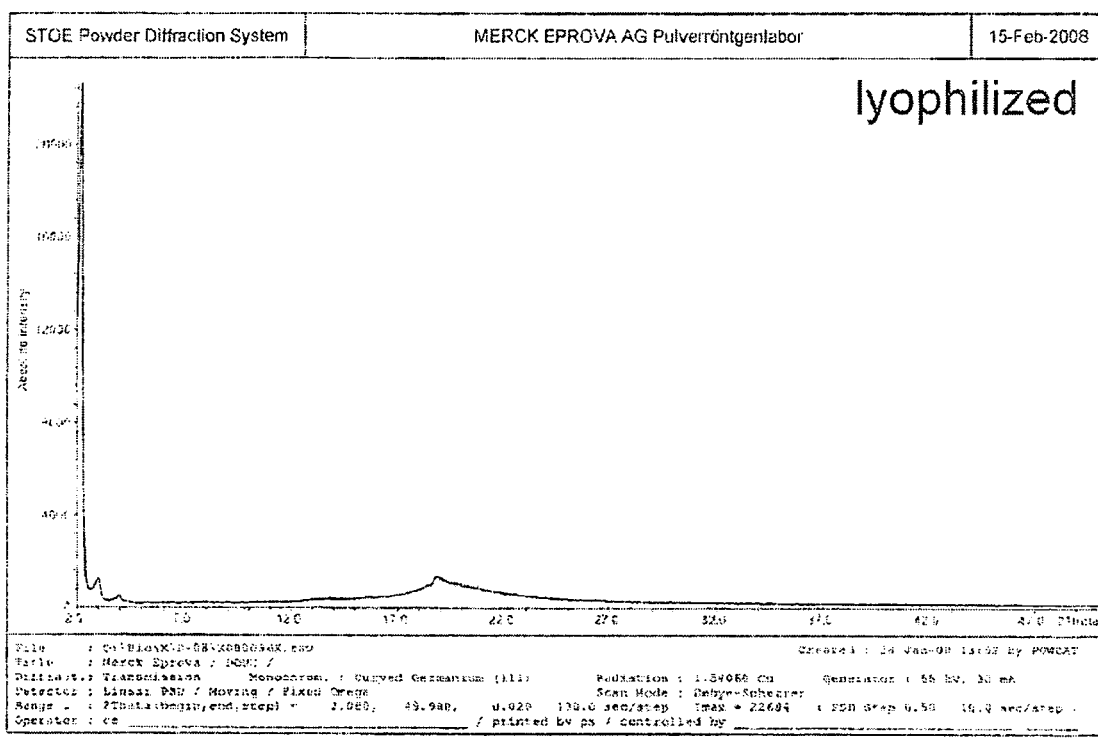
FIG. 2 Illustrates, for comparison, XRD spectrum of lyophilised DOPC.
Figure 3:
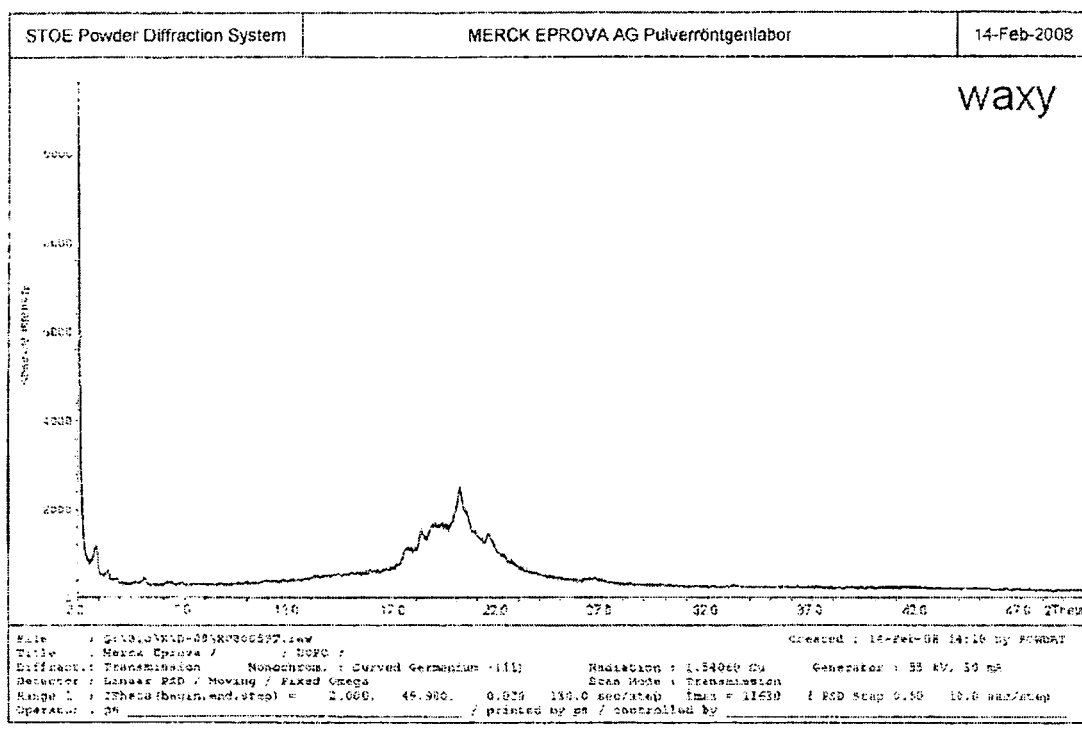
FIG. 3 Illustrates, for comparison, XRD spectrum of waxy DOPC.

An illustrative spectrum can be seen in FIG. 1 (type I). For comparison, spectra of commercially available, amorphous samples are likewise recorded under analogous conditions and shown as FIG. 2 (lyophilised) and FIG. 3 (waxy).

Table 2 lists selected 2 theta values for the type I DOPC crystal modification:

TABLE 2

| Type   |          | Selected 2 theta values                                                              |
|--------|----------|--------------------------------------------------------------------------------------|
| Type I | (R)-DOPC | 3.6, 5.3, 7.1, 8.8, 11.0, 12.3, 15.3, 17.6, 18.3, 19.3, 20.4, 21.1, 21.7, 22.8 and 26.4 |

Example 4

Modifications

Figure 4:
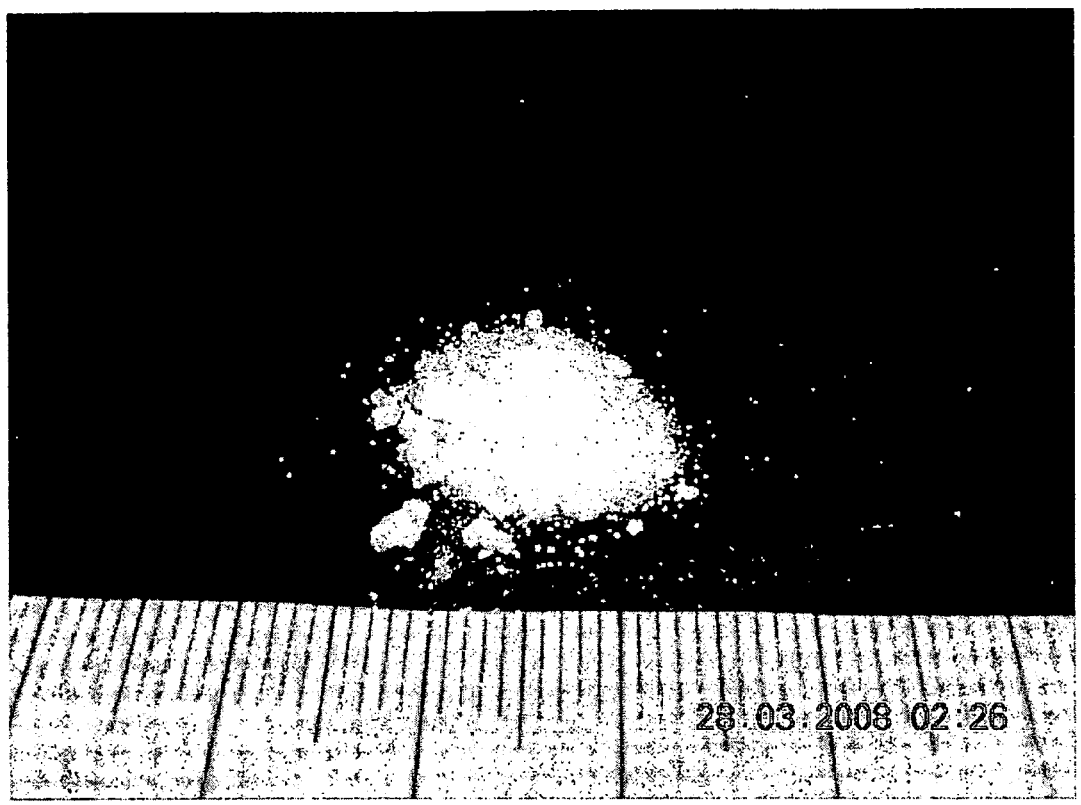
FIG. 4 Illustrates Type I DOPC crystal modifications produced as granular loose material.
Figure 5:
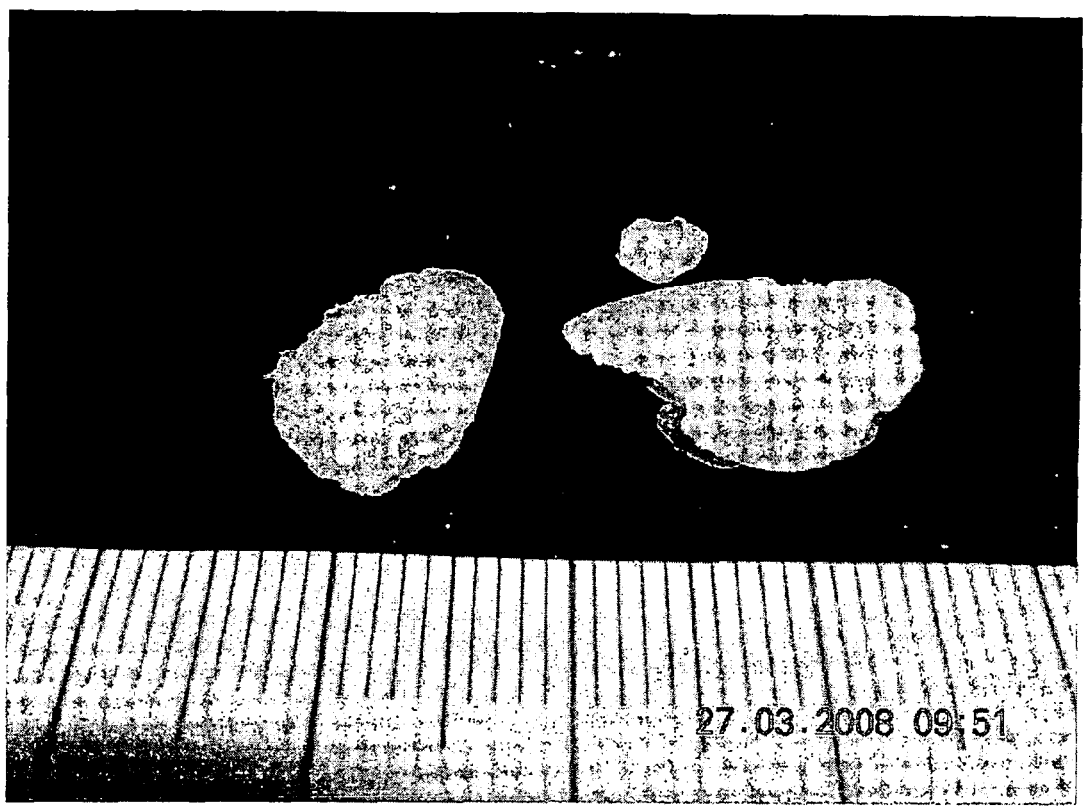
FIG. 5 Illustrates commercial DOPC samples obtained either as lyophilisate or as waxy lumps.

Type I DOPC crystal modifications are produced as granular loose material (FIG. 4), while commercial DOPC samples are obtained either as lyophilisate or as waxy lumps (FIG. 5).

Figure 6:
FIG. 6 Illustrates, under a polarizing microscope, the type I DOPC crystal modification.
Figure 7:
FIG. 7 Illustrates lyophilised DOPC under a polarizing microscope.
Figure 8:
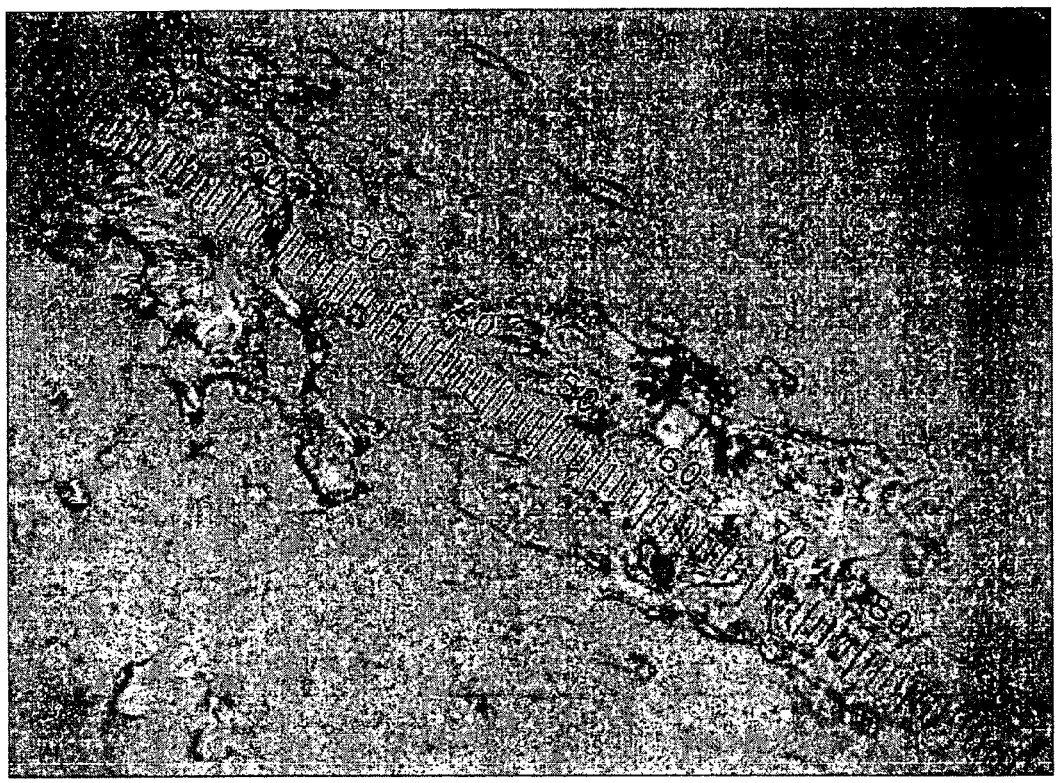
FIG. 8 Illustrates Waxy DOPC under a polarizing microscope.

Under the polarising microscope, the type I DOPC crystal modification is clearly evident as crystalline material (FIG. 6), while the lyophilised (FIG. 7) and waxy comparative materials (FIG. 8) appear amorphous.

Example 5

Melting Behaviour

Figure 9:
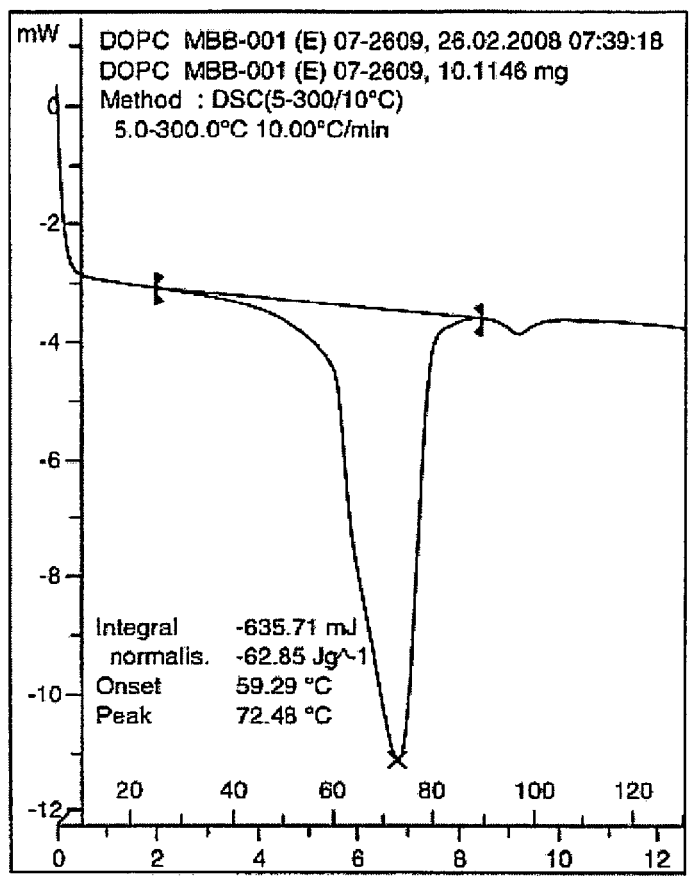
FIG. 9 Illustrates Melting behaviour of type I DOPC by differential scanning calorimetry (DSC) measurements.

Differential scanning calorimetry (DSC) measurements likewise show clear differences for the type I DOPC crystal modification (FIG. 9) and the lyophilised (FIG. 10) and waxy comparative material (FIG. 11).

The invention claimed is:

1. Crystalline (R,S)-, (R)- or (S)-DOPC.
2. Crystalline (R)- or (S)-DOPC.
3. A mixture of crystalline (R)- and crystalline (S)-DOPC.
4. Crystalline (R)-DOPC.
5. Crystalline (R)- or (S)-DOPC according to claim 2 having five of the 2 theta values 3.6, 5.3, 7.1, 8.8, 11.0, 12.3, 15.3, 17.6, 18.3, 19.3, 20.4, 21.1, 21.7, 22.8 and 26.4.
6. Crystalline (R)- or (S)-DOPC according to claim 2 having 2 theta values of 3.6, 5.3, 18.3, 19.3 and 21.7.
7. Crystalline (R)- or (S)-DOPC according to claim 2 having 2 theta values of 3.6, 5.3, 7.1, 12.3, 17.6, 18.3, 19.3, 21.1, 21.7 and 22.8.
8. Crystalline (R)- or (S)-DOPC according to claim 2 having a spectrum according to FIG. 1.
9. Crystalline (R)- or (S)-DOPC according to claim 1 having a melting point of greater than 60° C. and an enthalpy of melting of greater than 48 J/g.
10. A process for preparing a crystal modification of (R,S)-, (R)- or (S)-DOPC, comprising crystallizing from one or more aprotic solvents.
11. A process for preparing a crystal modification of (R,S)-, (R)- or (S)-DOPC according to claim 10, wherein the aprotic solvent is an ether.
12. A process for preparing a crystal modification of (R,S)-, (R)- or (S)-DOPC according to claim 10, wherein the aprotic solvent is a ketone.
13. A process for preparing a crystal modification of (R,S)-, (R)- or (S)-DOPC according to claim 10, wherein the aprotic solvent is a nitrile.
14. A process for preparing a crystal modification of (R,S)-, (R)- or (S)-DOPC according to claim 10, wherein the polar solvent is an ester selected from the group consisting of ethyl formate, methyl acetate, ethyl acetate, propyl acetate, isopropyl acetate, butyl acetate, isobutyl acetate, dimethyl carbonate, diethyl carbonate, 1,3-dioxolidin-2-one, and mixtures thereof.
15. A process according to claim 10, wherein the one or more aprotic solvents is in a mixture with an alcohol selected from the group consisting of methanol, ethanol, n-propanol, isopropanol, n-butanol, isobutanol, 2-butanol, tert-butanol, 3-methyl-1-butanol, ethylene glycol, methoxyethanol, ethoxyethanol, and mixtures thereof.
16. A process, according to claim 10, wherein the crystallization is carried out directly from a reaction solution without prior purification.
17. A process according to claim 10, which further comprises a recrystallization of amorphous or crystalline (R,S)-, (R)- or (S)-DOPC.
18. A method of achieving a medical effect in administering DOPC, comprising administering a crystal modification of (R,S)-, (R)- or (S)-DOPC, alone or optionally in a mixture with one or more lipids.
19. A pharmaceutical composition, comprising a crystal modification of (R,S)-, (R)- or (S)-DOPC and a pharmaceutically acceptable carrier.
20. A pharmaceutical composition according to claim 19, further comprising a further active compound selected from the group consisting of peptides, nucleotides, vaccines and cytostatics.
21. A pharmaceutical composition according to claim 19, which comprises one or more liposomes, lipoplexes, nanoparticles or microemulsions.
22. A process for preparing a crystal modification of (R,S)-, (R)- or (S)-DOPC according to claim 10, wherein the aprotic solvent is tetrahydrofuran, methyltetrahydrofuran or dioxane.
23. A process for preparing a crystal modification of (R,S)-, (R)- or (S)-DOPC according to claim 10, wherein the aprotic solvent is acetone, 2-butanone, methyl isobutyl ketone or methyl isopropyl ketone.
24. A process for preparing a crystal modification of (R,S)-, (R)- or (S)-DOPC according to claim 10, wherein the aprotic solvent is acetonitrile.

* * * * *